(12) United States Patent
Farley

(10) Patent No.: US 6,511,423 B2
(45) Date of Patent: Jan. 28, 2003

(54) CROSS BAR FOR A SURGICAL RETRACTOR SYSTEM

(75) Inventor: Daniel K. Farley, Traverse City, MI (US)

(73) Assignee: Thompson Surgical Instruments, Inc., Traverse City, MI (US)

( * ) Notice: Subject to any disclaimer, the term of this patent is extended or adjusted under 35 U.S.C. 154(b) by 0 days.

(21) Appl. No.: 09/761,631

(22) Filed: Jan. 17, 2001

(65) Prior Publication Data

US 2002/0095071 A1 Jul. 18, 2002

(51) Int. Cl.⁷ ................................................. A61B 1/32
(52) U.S. Cl. ........................ 600/231; 600/232; 600/235
(58) Field of Search ................................. 600/102, 228, 600/230, 231, 233, 234, 235, 210, 201; 24/490, 542, 535; 403/131, 118, 261; 248/904

(56) References Cited

U.S. PATENT DOCUMENTS

| | | | | |
|---|---|---|---|---|
| 3,572,326 A | | 3/1971 | Jensen | 128/20 |
| 4,143,652 A | * | 3/1979 | Meier et al. | 600/231 |
| 4,510,926 A | * | 4/1985 | Inaba | 600/102 |
| 4,617,916 A | | 10/1986 | LeVahn et al. | 128/20 |
| 4,813,401 A | * | 3/1989 | Grieshaber | |
| 5,228,429 A | * | 7/1993 | Hatano | 600/102 |
| 5,795,291 A | * | 8/1998 | Koros et al. | 600/232 |
| 5,876,325 A | * | 3/1999 | Mizuno et al. | 600/102 |
| 5,897,087 A | | 4/1999 | Farley | 248/229.21 |
| 5,984,867 A | * | 11/1999 | Deckman et al. | 600/232 |
| 6,017,008 A | | 1/2000 | Farley | 248/229.21 |
| 6,033,363 A | | 3/2000 | Farley et al. | 600/234 |
| 6,102,850 A | * | 8/2000 | Wang et al. | 600/102 |

* cited by examiner

Primary Examiner—Pedro Philogene
(74) Attorney, Agent, or Firm—McAndrews, Held & Malloy, Ltd.

(57) ABSTRACT

A surgical retractor system comprises a retractor frame secured to an operating structure. The retractor frame includes a cross bar that comprises a plurality of pivotally connected cross bar sections.

9 Claims, 3 Drawing Sheets

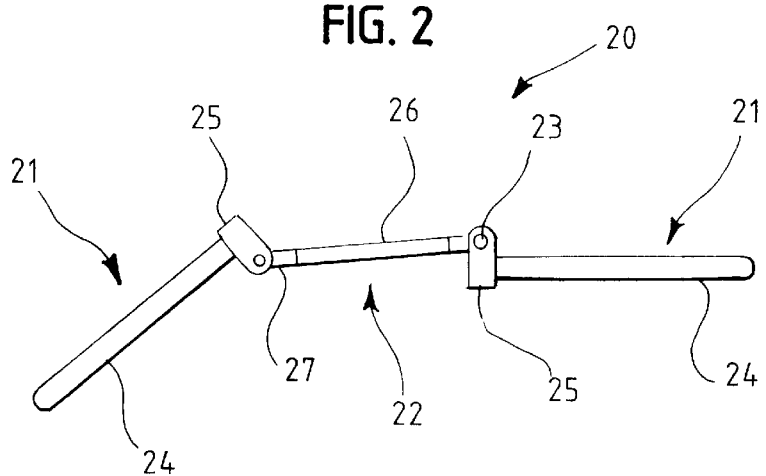
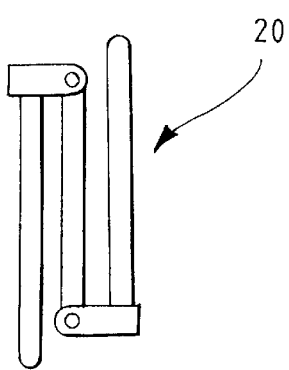
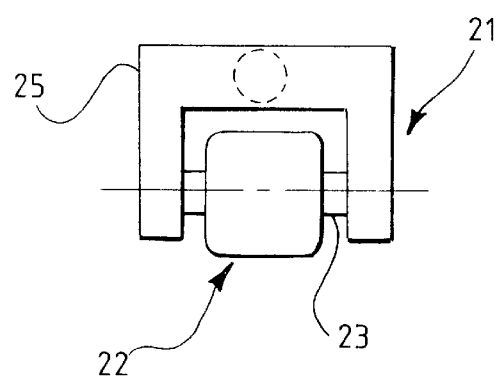
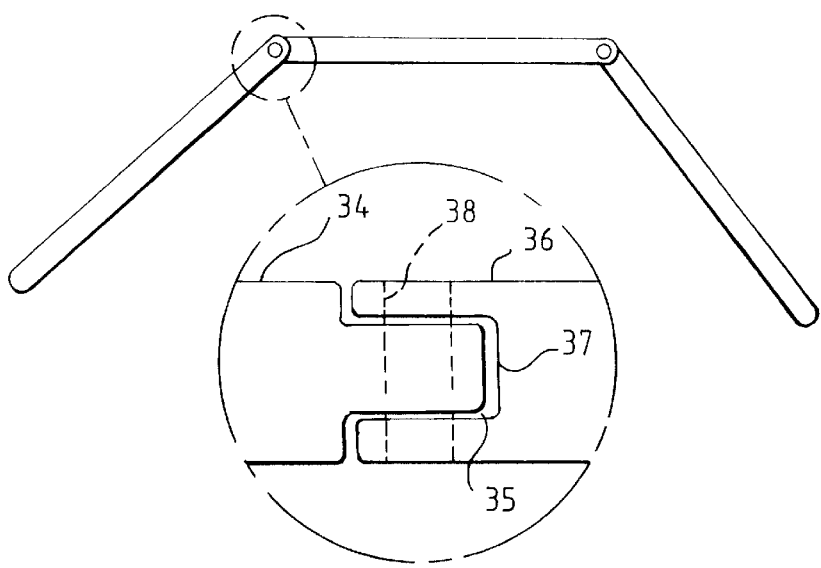

CROSS BAR FOR A SURGICAL RETRACTOR SYSTEM

BACKGROUND OF THE INVENTION

The present invention relates to surgical apparatus for retracting anatomy to provide exposure of the operative site, and more particularly relates to a retraction apparatus that is sturdy, adjustable, and conducive to thorough sterilization.

During surgical procedures, a surgeon will typically make an incision in a patient to access the sites of interest, such as internal organs and bone structures, for a particular procedure. A surgical retractor system is typically utilized to maintain clear access to the site of interest. Retractors are designed to hold back the anatomy in the immediate area of the operative site to enable a surgeon to have both an optimal view of the site and a sufficiently open area within which to work.

The usefulness of any retractor device is necessarily limited by the number of ways that the retractor can be positioned with respect to the retracted anatomy as well as the ease with which the surgeon can adjust the relative position of the retractor both before and during surgery. The less obstructive and more versatile a retractor device is, the more desirable it becomes for use in the above-described manner. Thus, variance in types of surgery and patient size necessitates surgical retractor systems that are adjustable. In addition, equipment sterilization requirements call for a device that can be thoroughly cleansed by conventional means in a safe and easy manner.

A surgical retractor system typically consists of a rail clamp, a frame connected to the rail clamp, and retractor blades that are clamped to the frame. The rail clamp is commonly secured to an operating table and provides a fixed and sturdy support for the frame and the retractor blades. Each of the components in a typical surgical retractor system is conventionally made of stainless steel, although, as disclosed in U.S. Pat. No. 6,033,363, parts of the system may be made from a nonconductive material. The reason that stainless steel is generally used is that stainless steel is easily sterilized. As would be expected, before any use of the surgical retractor system can be made during a surgical procedure, the system must be thoroughly sterilized for the protection of the patient. This sterilization is performed in the standard methods well known in the art.

Often, a surgical retractor system frame includes one or more posts, each connected to the operating table by a rail clamp. Typically, some form of support structure for supporting retractor blades is connected to the post(s) by clamps. Prior art support structures include individual straight support arms joined to each other and/or the frame with clamps. Because their use can involve aligning multiple pieces and connecting the pieces with clamps, their set up during a surgical procedure can be time consuming. Additionally, such a system can have a number of arms and clamps that must be sterilized before every procedure, and stored between uses.

Some past prior art retractor systems, such as the one disclosed in U.S. Pat. No. 4,617,916, include bent support arms. While eliminating the need for a clamp at the portion between bends in the arm, these systems cannot be repositioned or adjusted, thereby reducing the flexibility and versatility of these systems. Additionally, the large bent support arms are difficult to store, and may not fit in standard sterilization cases.

It is therefore an object of the present invention to provide an improved surgical retractor.

It is therefore an object of the present invention to provide a surgical retractor system having a retractor frame that will facilitate precise placement of retractor blades relative to the patient.

It is a further object of the present invention to provide a surgical retractor system that will be sturdy as well as easy to sterilize and store.

SUMMARY OF THE INVENTION

These and other objects of the present invention are achieved in a surgical retractor system that retracts anatomy during all types of surgery. The system is particularly applicable to morbid obese and liver procedures. The system includes a retractor frame secured to an operating structure, such as an operating table. Retractor blades are supported by the retractor frame. The retractor frame includes a cross bar. The cross bar comprises a plurality of cross bar sections. Each of the cross bar sections is pivotally connected to its adjacent cross bar section(s).

BRIEF DESCRIPTION OF THE DRAWINGS

FIG. 2 is an elevation view of a cross bar comprising pivotally connected cross bar sections.

FIG. 3 is an elevation view of a cross bar comprising pivotally connected cross bar sections folded for storage.

FIG. 4 is a sectional view of a cross bar comprising pivotally connected cross bar sections.

FIG. 5 provides views of the pivotally connected cross bar sections of an alternate embodiment.

DETAILED DESCRIPTION OF A PREFERRED EMBODIMENT

Figure 1:
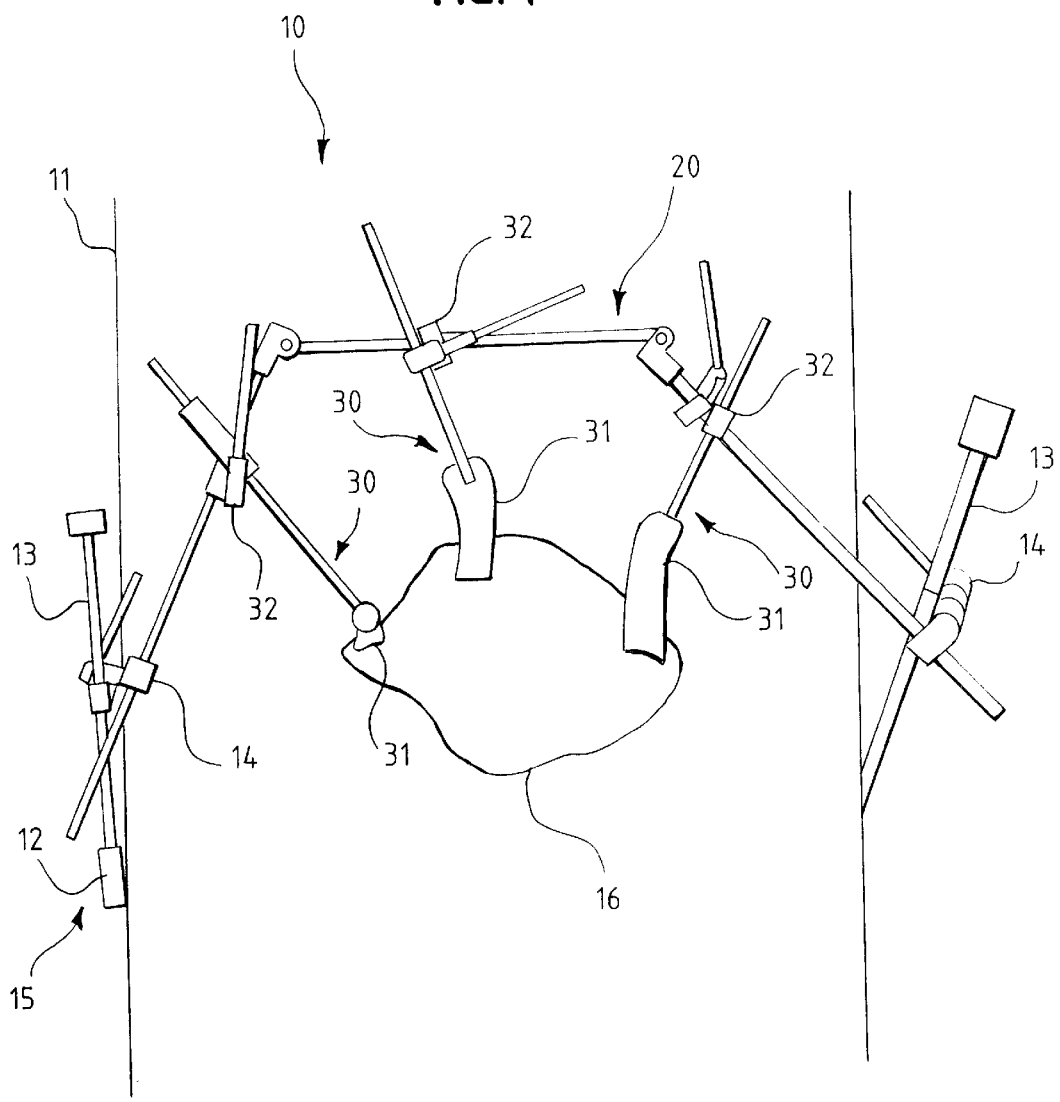
FIG. 1 is a perspective view of a surgical retractor system with a cross bar comprising pivotally connected cross bar sections.

FIG. 1 shows a surgical retractor system 15. The system may be used to retract anatomy to provide exposure to a site for operation. During a surgical procedure, an incision 16 is made to access a site of interest in the patient. The retractor system is then used to retract anatomy to allow continued access to the site of interest.

The surgical retractor system 15 comprises a retractor frame 10. The retractor frame may be mounted to an operating structure 11 by the use of a frame clamp 12. The operating structure 11 is often an operating table, but could conceivably be a stretcher or some other surface.

The embodiment of the system illustrated by FIG. 1 is particularly well adapted for use during morbid obesity surgical procedures. The illustrated embodiment's retractor frame 10 may include two posts 13. Each post 13 is mounted to the operating structure 11 by frame clamp 12. The two posts 13 may be mounted on opposite sides of the operating structure 11 for stability. Preferably, the frame clamp 12 is a rail clamp that is secured to the operating structure 11 over the sterile drapes (not shown) from within the sterile field. The illustrated posts 13 may extend generally vertically, and a cross bar 20 may be secured to the posts 13 with post clamps 14. The post clamps 14 allow for precise placement of the cross bar 20 vertically along the posts 13 as well as angular adjustment relative to the posts 13. The cross bar 20 may be used to connect components of the retractor frame 10. In the illustrated embodiment, the cross bar 20 traverses the width of the operating structure 11, connecting the two posts 13 and also providing a mounting point for the retractors 30. The retractors 30 comprise retractor blades 31 that may be placed in the incision 16 and serve to hold it open, thereby providing access to the operative site. The retractors 30 may mount on the cross bar 20 through the use of retractor clamps 32.

As shown in FIG. 2, the cross bar 20 of the illustrated embodiment comprises three cross bar sections 21, 22. The cross bar sections 21, 22 may be substantially straight and are pivotally attached or connected to adjacent cross bar sections by pins 23. Use of a cross bar divided into pivotally connected sections provides a cross bar that is flexible and adjustable while still maintaining adequate rigidity. Such a cross bar is also quick and simple to adjust and place, and improves the ease of assembly of the retractor system. The pivotal attachment or connection may be a permanent connection between adjacent sections or a temporary connection so long as the adjacent bar sections are pivotally fixed relative to each other, and the cross bar provides for a rigid frame during use.

The illustrated embodiment includes two end sections 21. Each of the end sections 21 has a straight portion 24 and an end portion 25. The end portion 25 may be integral with the cross bar section 21, 22 or may be detachable. A detachable end portion 25 may be used to permit a conventional prior art cross bar section to be used as a component of the present invention. Persons skilled in the art will appreciate that a detachable end portion 25 can be connected to a conventional prior art cross bar section by methods well known in the art. The straight portion 24 may provide a surface for mounting clamps. The retractor system 15 may use clamps similar to those disclosed in U.S. Pat. Nos. 5,897,087 and 6,017,008. Preferably, and to accommodate standard clamps, the straight portion 24 in the embodiment illustrated may have a circular cross-section with a ½" nominal diameter. The length of the sections is determined by the width of the operating structure and the size of the patient. In the illustrated embodiment, the end sections 21 are about 12.5" in length, which is the preferred length.

As shown in FIG. 4, the end portion 25 comprises a yoke configured to accept the middle section 22. The pin 23 may be located in the end portion 25, with the pin's center offset from the longitudinal centerline of the straight portion 24. This pin placement allows the cross bar 20 to fold in a compact manner, with the cross bar sections 21, 22 in close proximity and close to parallel with each other when the cross bar 20 is in the folded position, as shown in FIG. 3.

Returning to FIG. 2, the illustrated cross bar 20 may include a middle section 22. The middle section 22 in turn comprises a central portion 26 and two end portions 27. As with the straight portion 24 of the end section 21, the central portion 26 of the middle section 22 facilitates clamp mounting. Similarly, the illustrated embodiment's central portion 26 of the middle section 22 may have a cross section nominally ½" in diameter. The end portions 27 of the middle section 22 may have flat surfaces opposite each other for fitting in the yoke of the end portion 25 of end section 21. The illustrated embodiment's middle section 22 is about 10" in length, which is the preferred length. The hole for pin 23 is located along the longitudinal centerline of the middle section 22. When the middle section 22 just described is assembled as illustrated in FIG. 2 and FIG. 3 in conjunction with the end sections 21 described above, the resulting cross bar 20 can be folded for compact storage. For example, the illustrated cross bar can extend to a length of about 34" and fold to a size of about 15"×2".

As mentioned above, the pivotal attachment or connection may be a permanent connection between adjacent sections or a temporary connection so long as the adjacent bar sections are pivotally fixed relative to each other, and the cross bar provides for a rigid frame during use. One alternate embodiment of the pivotal connection is shown in FIG. 5. In the particular embodiment illustrated, first cross bar section 34 and second cross bar section 36 are pivotally connected by pin 38. First cross bar section 34 has a tab 35 configured for slot 37 in second cross bar section 36. The cross bar sections of this particular embodiment provide for improved ease of manufacturing, as each section may be machined from a single bar.

Figure 6:
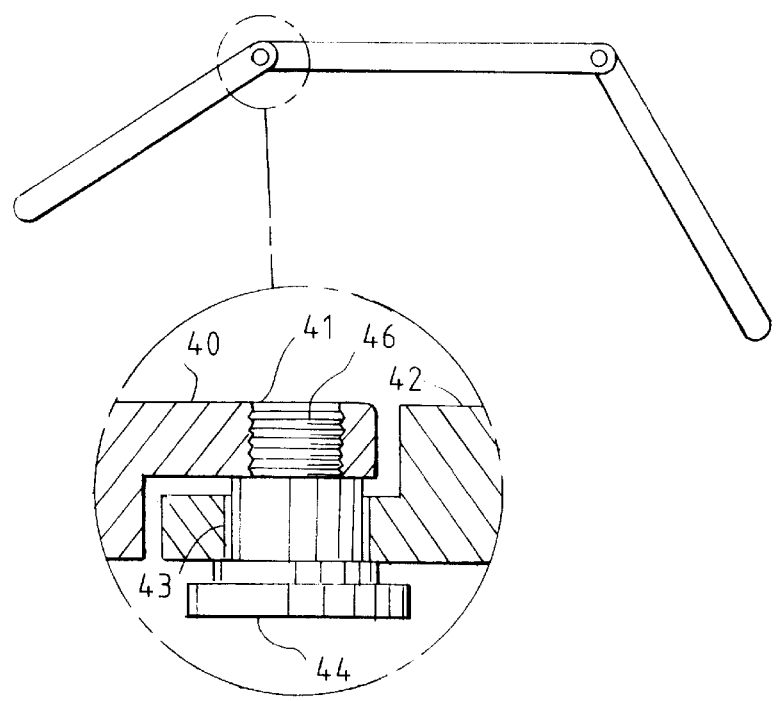
FIG. 6 provides views of the pivotally connected cross bar sections of an alternate embodiment.

FIG. 6 shows another embodiment featuring a different type of pivotal attachment between cross bar sections. In this particular embodiment, first cross bar section 40 includes a threaded portion 41. Second cross bar section 42 comprises a hole 43. Removable pin 44 includes a threaded end 46 that engages the threaded portion 41 of the first cross bar section 40. The threaded connection with the first cross bar section 40 holds the removable pin 44 in place. Removable pin 44 may be quickly and easily removed by unscrewing it from the threaded engagement with the first cross bar section 40.

Figure 7:
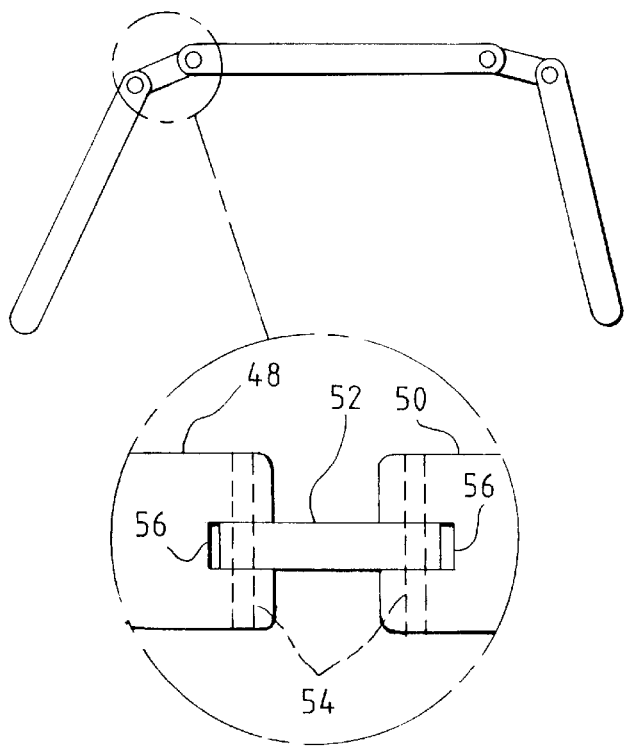
FIG. 7 provides views of the pivotally connected cross bar sections of an alternate embodiment.

FIG. 7 shows yet another possible embodiment. In this particular embodiment, first cross bar section 48 and second cross bar section 50 are connected by means of a link 52. The link 52 is connected to the cross bar sections 48, 50 by pins 54. The link 52 may be of a lesser width than the cross bar sections 48, 50 and fit into slots 56 as shown.

In addition to facilitating folding for easy storage, a cross bar featuring sections pivotally connected also provides for flexibility and adjustability when the retractor system is in use. By allowing the different sections of the cross bar to be adjusted relative to each other at the pivot joints, the system can be adjusted to accommodate different patient sizes. Additionally, the cross bar and/or a retractor system including the cross bar may be used for many different procedures. For example, the cross bar is also particularly well suited for use in liver transplant and resection procedures. The use of retractor clamps along the surface of the cross bar provides for further adjustability in the placement of the retractors for each patient/procedure. While allowing for adjustability and versatility in use, the cross bar is still rigid enough when clamped in place to function properly.

By allowing the versatility and adjustment made possible by the use of pivot joints in the cross bar, the need for a multitude of clamps joining individual frame components is reduced without the sacrifices in flexibility and storage space imposed by large, bent support arms. This reduction in clamp number eases assembly and reduces assembly time. Further, it results in fewer parts to store.

In addition to the benefits in adjustability, assembly, and storage, the cross bar can also make sterilization easier. Reducing the number of parts used also reduces the number of parts to be sterilized. Moreover, some clamps have intricate construction that must be disassembled for sterilization and reassembled later. Reducing the number of clamps also reduces this need for disassembly and reassembly. Furthermore, a foldable cross bar can also fit in a standard sterilization case, further easing sterilization.

While particular embodiments of the invention have been shown, it will be understood that the invention is not limited thereto since modifications may be made by those skilled in the art, particularly in light of the foregoing teaching. For instance, using a different number of cross bar sections (e.g., two, or four or more) or having one or more bent cross bar sections may be more desirable for different retractor systems. A different cross section may be used to accommodate a different clamping system. The cross bar may be joined to different parts of a retractor system than the posts. These and other modifications may be made. It is, therefore, the appended claims that define the true spirit and scope of the invention.

What is claimed is:

1. A surgical retractor system comprising a retractor frame, said retractor frame comprising a cross bar and two posts, said cross bar secured to each of said two posts; said cross bar comprising a plurality of cross bar sections, said cross bar sections pivotally connected to adjacent cross bar sections, said cross bar sections being substantially straight along their longitude;

at least two frame clamps for securing said retractor frame to an operating structure; and a retractor blade connected to said cross bar.

2. The surgical retractor system of claim 1, wherein said cross bar further comprises at least one pin for pivotally connecting said cross bar sections.

3. The surgical retractor system of claim 1, wherein said surgical retractor system further comprises a retractor clamp, wherein said retractor blade is connected to said cross bar with said retractor clamp.

4. The surgical retractor system of claim 1, wherein said cross bar comprises three said cross bar sections.

5. The surgical retractor system of claim 1, wherein said surgical retractor system is for use with liver or morbid obesity procedures.

6. A cross bar for a surgical retractor system, said cross bar connecting components of a retractor frame; and comprising a plurality of cross bar sections, said cross bar sections pivotally connected to adjacent cross bar sections, said cross bar sections comprising a plurality of clamp mounting surfaces along the length of said cross bar, said cross bar sections being substantially straight along their longitude.

7. The cross bar of claim 6, wherein said cross bar further comprises at least one pin for pivotably connecting said cross bar sections.

8. The cross bar of claim 6, wherein said surgical retractor system further comprises a retractor clamp, wherein said retractor blade is connected to said cross bar with said retractor clamp.

9. The cross bar of claim 6, wherein said cross bar comprises three said cross bar sections.

* * * * *